(12) United States Patent  (10) Patent No.: US 9,276,300 B2
Mueller  (45) Date of Patent: Mar. 1, 2016

(54) SURGICAL INSTRUMENTS

(71) Applicant: COVIDIEN LP, Mansfield, MA (US)

(72) Inventor: Peter M. Mueller, Frederick, CO (US)

(73) Assignee: Covidien LP, Mansfield, MA (US)

( * ) Notice: Subject to any disclaimer, the term of this patent is extended or adjusted under 35 U.S.C. 154(b) by 148 days.

(21) Appl. No.: 14/065,902

(22) Filed: Oct. 29, 2013

(65) Prior Publication Data
US 2014/0148799 A1 May 29, 2014

Related U.S. Application Data

(60) Provisional application No. 61/730,405, filed on Nov. 27, 2012.

(51) Int. Cl.
| H01M 10/6563 | (2014.01) |
| A61B 17/32 | (2006.01) |
| A61B 18/14 | (2006.01) |
| H01M 10/613 | (2014.01) |
| H01M 10/623 | (2014.01) |
| A61B 18/18 | (2006.01) |
| A61B 18/20 | (2006.01) |
| A61B 18/00 | (2006.01) |
| A61B 18/12 | (2006.01) |

(52) U.S. Cl.
CPC ... *H01M 10/6563* (2015.04); *A61B 17/320068* (2013.01); *A61B 17/320092* (2013.01); *A61B 18/1445* (2013.01); *H01M 10/613* (2015.04); *H01M 10/623* (2015.04); *A61B 18/1815* (2013.01); *A61B 18/20* (2013.01); *A61B 2018/00017* (2013.01); *A61B 2018/00095* (2013.01); *A61B 2018/1226* (2013.01); *A61B 2018/1823* (2013.01)

(58) Field of Classification Search
None
See application file for complete search history.

(56) References Cited

U.S. PATENT DOCUMENTS

| 5,004,382 | A | * | 4/1991 | Yoshino | 408/68 |
| 5,486,162 | A | | 1/1996 | Brumbach | |
| 5,562,609 | A | | 10/1996 | Brumbach | |
| 5,670,860 | A | | 9/1997 | Conrady et al. | |
| 5,704,934 | A | | 1/1998 | Neuwirth et al. | |
| 6,039,262 | A | * | 3/2000 | DeAnna | 236/93 R |
| 6,588,277 | B2 | | 7/2003 | Giordano et al. | |
| 6,689,087 | B2 | | 2/2004 | Pal et al. | |
| 7,270,910 | B2 | * | 9/2007 | Yahnker et al. | 429/62 |
| 7,273,483 | B2 | | 9/2007 | Wiener et al. | |
| 7,314,447 | B2 | | 1/2008 | Park et al. | |
| 7,336,486 | B2 | * | 2/2008 | Mongia | 361/695 |
| 7,372,348 | B2 | * | 5/2008 | Xu et al. | 335/78 |
| 7,527,086 | B2 | * | 5/2009 | Wang et al. | 165/104.31 |
| 2004/0263008 | A1 | * | 12/2004 | Voigt et al. | 310/58 |
| 2007/0141453 | A1 | * | 6/2007 | Mahalingam et al. | 429/120 |
| 2007/0185554 | A1 | | 8/2007 | Appling et al. | |
| 2008/0035361 | A1 | * | 2/2008 | Zhang | 173/217 |
| 2009/0131940 | A1 | | 5/2009 | Brunnett et al. | |
| 2009/0138006 | A1 | * | 5/2009 | Bales et al. | 606/33 |
| 2009/0143805 | A1 | * | 6/2009 | Palmer et al. | 606/169 |
| 2010/0198220 | A1 | * | 8/2010 | Boudreaux et al. | 606/52 |
| 2012/0115005 | A1 | * | 5/2012 | Stulen et al. | 429/120 |

* cited by examiner

Primary Examiner — Gary Jackson
Assistant Examiner — Nathan A Baldwin

(57) ABSTRACT

A surgical instrument includes a housing having a shaft extending therefrom. An end effector is operably supported at the distal end of the shaft includes a pair of jaw members. A generator operably coupled to the housing is in operable communication with a battery assembly of the surgical instrument to convert electrical energy into at least one of RF and ultrasonic energy to energize the at least one activatable jaw member. A thermally-activatable device in operable communication with either the generator or the battery assembly is configured to promote air-flow around the generator and battery assembly.

13 Claims, 3 Drawing Sheets

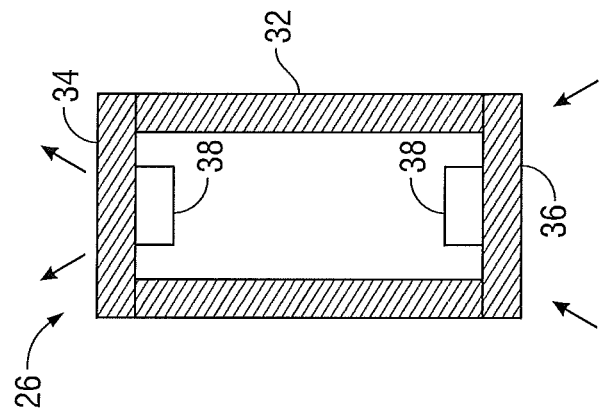
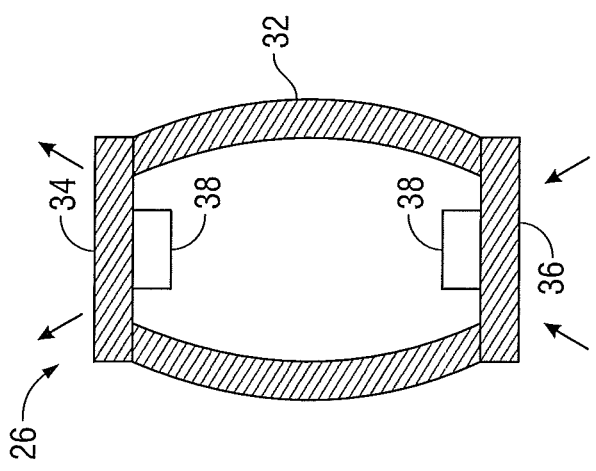
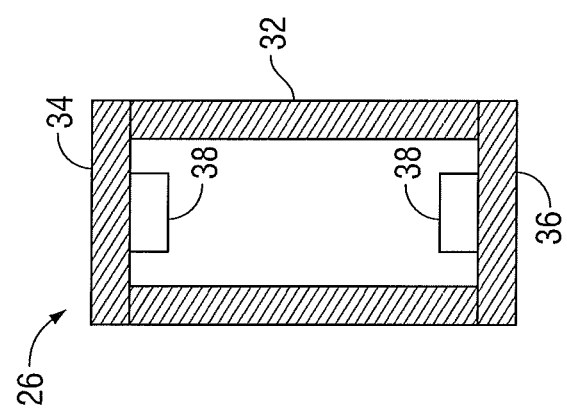

SURGICAL INSTRUMENTS

CROSS REFERENCE TO RELATED APPLICATION

The present application claims the benefit of and priority to U.S. Provisional Application Ser. No. 61/730,405, filed on Nov. 27, 2012, the entire contents of which are incorporated herein by reference.

BACKGROUND

1. Technical Field

The present disclosure relates to surgical instruments and, more particularly, to portable surgical instruments including a thermally-activatable heat pump configured to cool heat-dissipating components disposed within the portable surgical instrument.

2. Background of Related Art

Portable surgical instruments are known in the medical arts. Portable surgical instruments overcome some of the drawbacks that are typically associated with surgical instruments that draw power from electrical outlets. That is, outlet driven surgical instruments utilize power cords that may create tripping and/or entanglement hazards in an operating room environment.

Typically, the portable surgical instrument includes a battery or battery assembly that is configured to removably couple or "latch" to the portable surgical instrument. In addition, the portable surgical instrument may be configured to include one or more selectively removable generators that communicate with the battery assembly to provide energy to an end-effector assembly that is associated with the portable surgical instrument.

As is common with portable surgical instruments, during operation of thereof, the battery and/or generator (or components associated therewith) may rise in temperature such as, for example, during prolonged periods of use. As can be appreciated, an excessive rise in temperature of either of the battery or generator may cause damage thereto and/or other operative components in the vicinity thereof.

SUMMARY

As can be appreciated, a device capable of "cooling" or maintaining the battery and/or generator at a constant temperature may prove advantageous in the surgical environment.

In the drawings and in the descriptions that follow, the term "proximal," as is traditional, will refer to an end which is closer to the user, while the term "distal" will refer to an end that is farther from the user.

An aspect of the present disclosure provides a surgical instrument. The surgical instrument includes a housing including an elongated shaft that extends distally from the housing. An end effector operably supported at the distal end of the elongated shaft includes a pair of jaw members. A generator operably coupled to the housing is in operable communication with a battery assembly of the surgical instrument to convert electrical energy into either RF or ultrasonic energy to energize the end effector. A thermally-activatable device in operable communication with either the generator or the battery assembly is configured to expand and contract due to changes in temperature thereof to promote air-flow around the generator and battery assembly such that the generator and battery are actively-cooled during use of thereof.

According to an aspect of the present disclosure, the thermally-activatable device may be a bi-metal pump. In certain instance, the bi-metal pump may be made from two or more strips of metal that have been joined via one of riveting, brazing and welding. Suitable metals may include, but are not limited to steel, copper or brass. The two or more strips of metal may be formed into a generally cylindrical drum configuration having sidewalls coupled to top and bottom walls.

A heat sink may be operably associated with each of the generator and battery assembly. In this instance, expansion and contraction of the thermally-activatable device is caused by the heat sink such that expansion of the thermally-activatable device draws air therein and contraction of the thermally-activatable device expels air therefrom.

Two or more check-valves may be operably coupled to the thermally-activatable device and may be configured to allow an in-flow of air into the thermally-activatable device upon expansion thereof and may be configured to allow an out-flow of air from the thermally-activatable device upon contraction thereof.

According to a further aspect of the instant disclosure, the surgical device is either an electrosurgical device or an ultrasonic device.

An aspect of the present disclosure provides a surgical instrument. The surgical instrument includes a housing including an elongated shaft that extends distally from the housing. The elongated shaft is configured to pass through a cannula or body orifice and defines a longitudinal axis therethrough. An end effector operably supported at the distal end of the elongated shaft includes a pair of jaw members. A generator operably coupled to the housing is in operable communication with a battery assembly of the surgical instrument to convert electrical energy into either RF or ultrasonic energy to energize the at least one activatable jaw member. A thermally-activatable device operably disposed in the housing is in operable communication with the generator and the battery assembly. A heat sink may be operably associated with each of the generator and battery assembly. The thermally-activatable device is responsive to temperature change and configured to promote air-flow around the generator and battery assembly such that the generator and battery are actively-cooled during use of thereof.

According to an aspect of the present disclosure, the thermally-activatable device may be a bi-metal pump. In certain instance, the bi-metal pump may be made from two or more strips of metal that have been joined via one of riveting, brazing and welding. Suitable metals may include, but are not limited to steel, copper or brass. The two or more strips of metal may be formed into a generally cylindrical drum configuration having sidewalls coupled to top and bottom walls.

In certain instances, the thermally-activatable device may be configured to expand and contract due to changes in temperature thereof caused by the heat sink such that expansion of the thermally-activatable device draws air therein and contraction of the thermally-activatable device expels air therefrom.

Two or more check-valves may be operably coupled to the thermally-activatable device and may be configured to allow an in-flow of air into the thermally-activatable device upon expansion thereof and may be configured to allow an out-flow of air from the thermally-activatable device upon contraction thereof.

According to a further aspect of the instant disclosure, the surgical device is either an electrosurgical device or an ultrasonic device.

BRIEF DESCRIPTION OF THE DRAWINGS

Various embodiments of the present disclosure are described hereinbelow with reference to the drawings, wherein:

FIGS. 2A-2C are side views of the thermally-activatable device shown in various configurations.

DETAILED DESCRIPTION OF THE EMBODIMENTS

Detailed embodiments of the present disclosure are disclosed herein; however, the disclosed embodiments are merely examples of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

Thermally-activatable devices 26, 126 (FIGS. 1A and 1B) are configured for use with various handheld or portable surgical instruments (see FIGS. 1A and 1B) to maintain internal components of the portable surgical instruments within acceptable temperature ranges. For illustrative purposes, thermally-activatable devices 26, 126 are described in terms of use with an electrosurgical forceps 2 and an ultrasonic instrument 102, see FIGS. 1A and 1B, respectively, although other devices are contemplated.

Figure 1A:
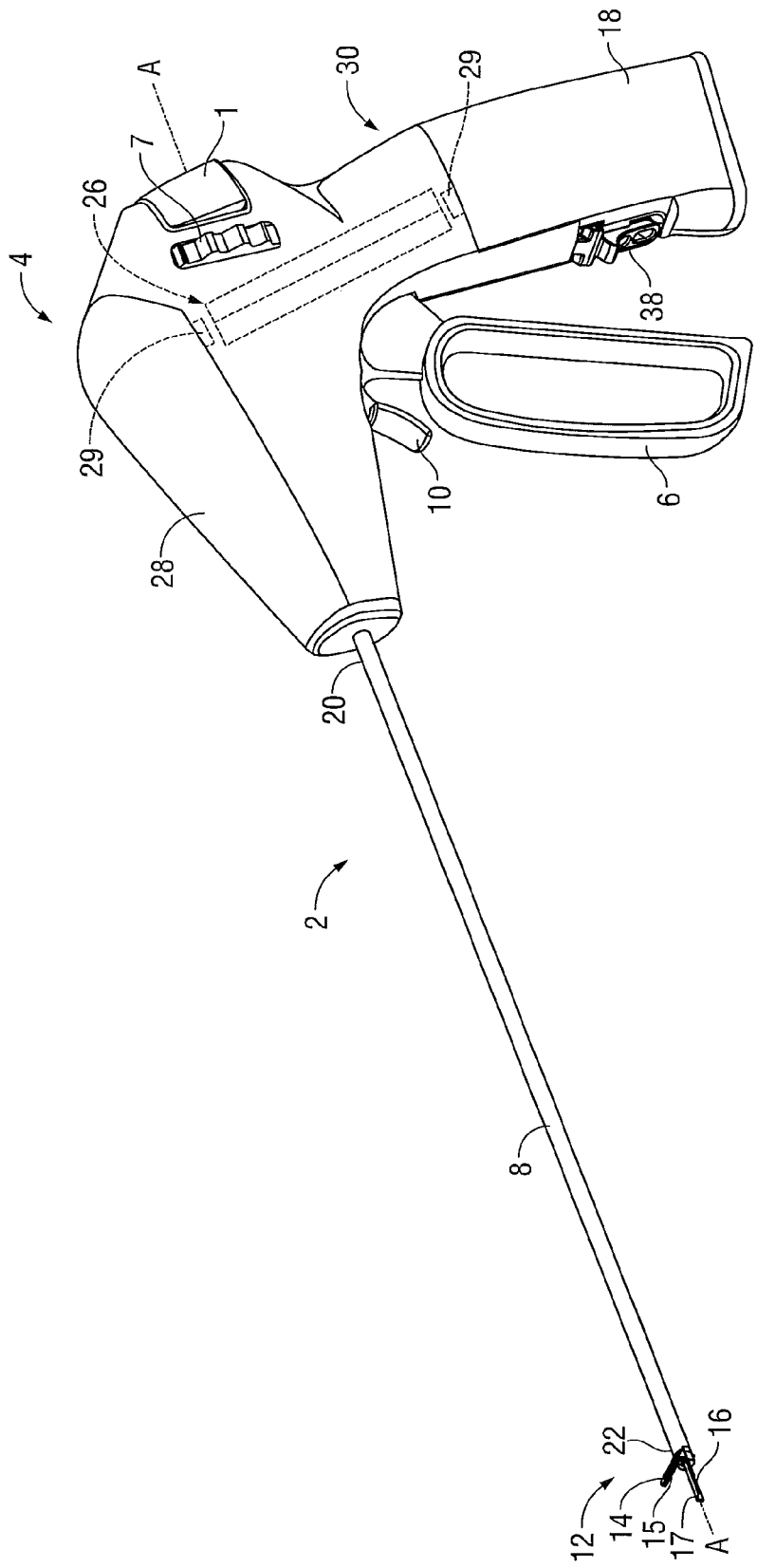
FIG. 1A is a side, perspective view of a battery-powered surgical instrument configured for use with a thermally-activatable device according to an embodiment of the present disclosure.

Continuing with reference to FIG. 1A, a bipolar electrosurgical forceps 2 (forceps 2) that is configured for use with the thermally-activatable device 26 is illustrated. Forceps 2 is shown configured for use with various electrosurgical procedures and generally includes a housing 4, a shaft 8, a battery assembly 18, a removable generator 28, a movable handle assembly 6, a rotating assembly 7, a trigger assembly 10, a drive assembly (not explicitly shown), and an end effector assembly 12. The end effector assembly 12 operatively connects to a distal end of the shaft 8 and, in turn, connects to the drive assembly which is actuatable to impart movement of one or both of a pair of jaw members 14, 16 of end effector assembly 12 to grasp or otherwise treat tissue. A distal end of the housing 4 is configured to support and/or couple to a proximal end 20 of shaft 8. Shaft 8 extends from housing 4 and defines a longitudinal axis "A-A" therethrough (FIG. 1A).

In one embodiment, jaw member 14 is pivotable about the jaw member 16 (and/or the distal end 22 of the shaft 8) and movable relative thereto when movable handle assembly 6 is moved proximally. More particularly, jaw member 14 is movable from an open configuration for positioning tissue between the jaw members 14 and 16, to a clamping configuration for grasping tissue between the jaw members 14 and 16. As noted above, the forceps 2 is a bipolar forceps, i.e., each of the jaw members 14 and 16 includes a respective seal plate 15 and 17 (FIG. 1A) that is configured to function as an active electrode (or activatable) and a return electrode. One or more electrical leads (not shown) connect to the generator 28, extend through the shaft 8 and connect to the seal plates 15 and 17. In certain instances, it may prove advantageous to utilize a forceps 2 that is monopolar. In this instance, one of the jaw members, e.g., jaw member 14 including seal plate 15, functions as an activatable electrode and a return pad (or other suitable device) may be positioned on a patient and utilized to function as the return electrode.

Battery assembly 18 is configured to releasably couple to the housing 4 by one or more suitable coupling methods. In particular, a release latch 38 (FIG. 1A) is operably disposed at a distal end of the battery assembly 18 and allows an end user to selectively remove the battery assembly 18 from the forceps 2.

Generator 28 (FIG. 1A,) operably couples to the housing 4 and may be selectively removable independently therefrom or in connection with removal of the battery assembly 18. Generator 28 is in operable communication with the battery assembly 18 to provide electrosurgical energy at one or more suitable frequencies to the end effector 12 including the jaw members 14 and 16 to electrosurgically treat tissue, e.g., seal tissue. In particular, generator 28 includes electronics that converts the electrical energy from the battery assembly 18 into an RF energy waveform to energize one or both of the jaw members 14 and 16. That is, the generator 28 transmits the RF energy to the seal plates 15 and 17 to electrosurgically treat tissue.

An activation button 1 (FIG. 1A) is disposed on housing 4 and is in operable communication with the generator 28. In particular, the activation button 1 is configured to selectively enable the generator 28 to generate and, subsequently, transmit RF energy to the seal plates 15 and 17 of the jaw members 14 and 16, respectively.

One or more heat sinks 29 are operably disposed in the housing 4 (or battery assembly 18) and are configured to remove heat from one or more of the internal components associated with the forceps 2. In the embodiment illustrated in FIG. 1A, two (2) heat sinks 29 are disposed in the housing 4 and are operably coupled to a respective one of the generator 28 and battery assembly 18, as best seen in FIG. 1A. This configuration of heat sinks 29 is suitable for the specific configuration of the forceps 2.

Figure 1B:
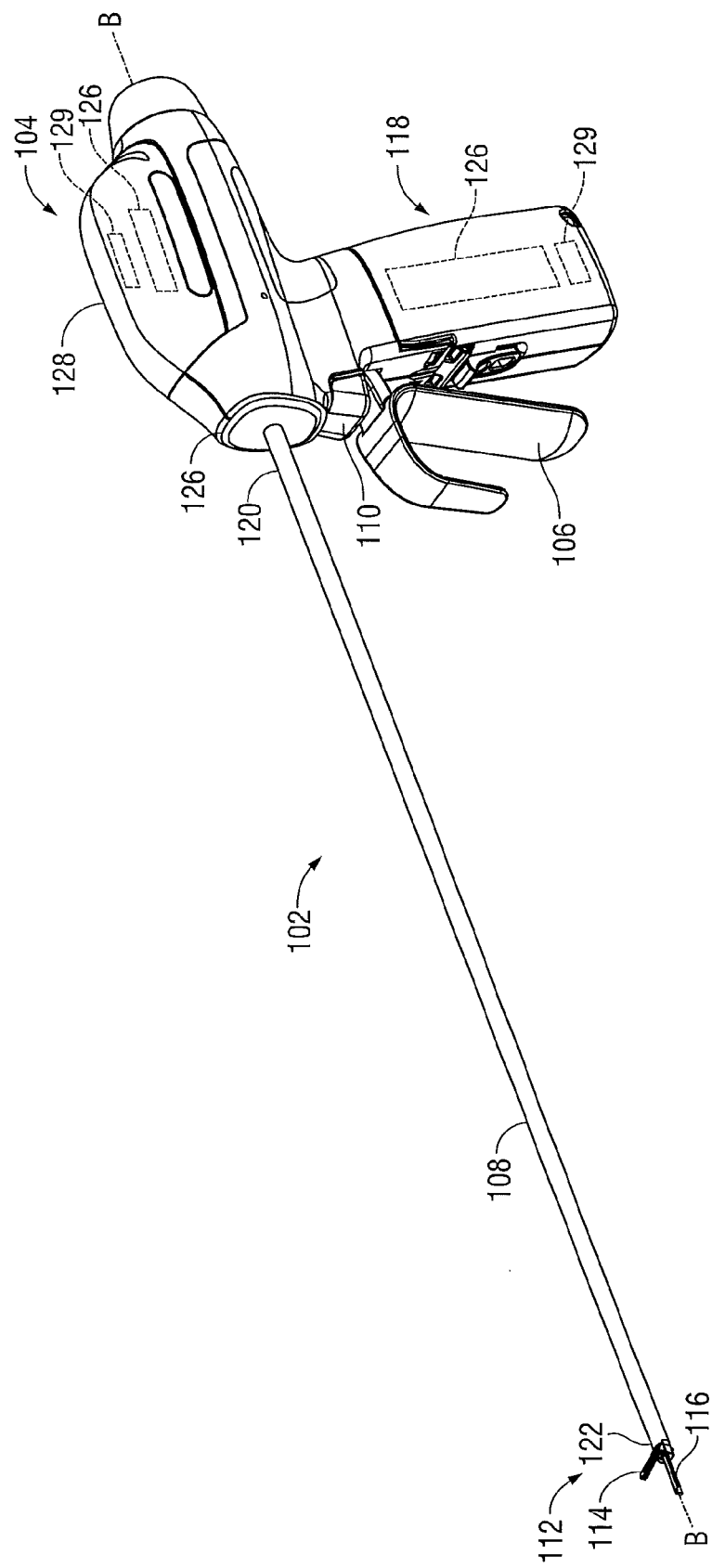
FIG. 1B is a side, perspective view of another type of battery-powered surgical instrument configured for use with the thermally-activatable device depicted if FIG. 1A.

With reference now to FIG. 1B, an ultrasonic instrument 102 that is configured for use with thermally-activatable device 126 is illustrated. Instrument 102 includes components similar to that of forceps 2. Briefly, ultrasonic instrument 102 includes a housing 104 configured to house one or more components, e.g., transducer, waveguide and electrical circuitry, that are configured for electrical communication with a battery assembly 118 of the instrument 102. A proximal end of housing 104 is configured to releasably couple to an ultrasonic generator 128 and the battery assembly 118. A distal end of the housing 104 is configured to support and/or couple to a proximal end 120 of a shaft 108. Shaft 108 extends from housing 104 and defines a longitudinal axis "B-B" therethrough (FIG. 1B). End effector 112 includes jaw members 114 and 116, wherein jaw member 114 is movable relative to jaw member 116 upon actuation of a movable handle assembly 106 that is coupled to housing 104. In the embodiment illustrated in FIG. 1B, jaw member 116 serves as an active or oscillating blade and is configured to effect tissue. An activation button 110 places the instrument 102 in two modes of operation, a low-power mode of operation and a high-power mode of operation. Unlike generator 28, generator 128 is configured to convert the electrical energy produced by the battery assembly 118 into ultrasonic energy.

More particularly, generator 128 includes a transducer (not shown) that is configured to convert electrical energy to mechanical energy that produces motion at an end of a waveguide (not shown) that is in operative communication with the active jaw member 116. When the transducer and waveguide are driven at their resonant frequency, they produce mechanical motion at the active jaw member 116. The electronics of the generator 128 converts the electrical energy from the battery assembly 118 into a high voltage AC waveform that drives the transducer. In one particular embodiment, the frequency of this AC waveform is the same as the resonant frequency of the waveguide and transducer. As can be appreciated, the magnitude of the AC waveform includes a value that produces the proper amount of mechanical motion.

As disclosed above with respect to the forceps 2, forceps 102 includes one or more heat sinks 129 that are operably disposed in the housing 104 (or battery assembly 118) and are configured to remove heat from one or more of the internal components associated with the ultrasonic instrument 102. In the embodiment illustrated in FIG. 1B, one (1) heat sink 129 is operably disposed in the housing 104 and one (1) heat sink 129 is operably disposed within the battery assembly 118. This configuration of heat sinks 129 is suitable for the specific configuration of the forceps 102.

Thermally-activatable devices 26, 126 are configured for use with forceps 2 and instrument 102, respectively. Thus, for purposes of brevity, only the operable features of the thermally-activatable device 26 are described in detail.

Thermally-activatable device 26 (device 26) is in operable communication with the generator 28 and the battery assembly 18 (FIG. 1A). Device 26 is configured to promote air-flow around one or both of generator 28 and battery assembly 18 such that generator 28 and battery assembly 18 do not exceed a threshold temperature or are maintained at a threshold temperature. With this purpose in mind, device 26 is positioned within the housing 4 and adjacent both heat sinks 29 of the generator and battery assembly (FIG. 1A).

In the illustrated embodiment, device 26 is made from two or more strips of suitable metal (e.g., bi-metal, tri-metal, tetra-metal, etc.) that have been joined via suitable methods, e.g., riveting, brazing and welding. Suitable metals may include, but are not limited to steel, copper and brass. For illustrative purposes, it is assumed that device 26 is made from two strips of steel and copper that have been welded together, i.e., a bi-metal. The strips of metal are formed into a housing 30 and include a generally cylindrical drum like configuration forming a "chamber" (FIGS. 2A-2C) defined by a sidewalls 32 coupled to top and bottom walls 34 and 36, respectively. In one particular embodiment, such as the one illustrated in FIGS. 2A-2C, the device 26 functions similar to that of a bi-metal pump.

One or more check valves 38 may be operably coupled or disposed on the device 26. In the illustrated embodiment, two (2) check valves 38 are operably coupled inside of the device 26 by one or more suitable coupling methods. Check valves 38 are configured to allow an in-flow of air into the device 26 upon expansion thereof and are configured to allow an out-flow of air from the device 26 upon contraction thereof. In embodiments, check valves 38 may be snap acting to allow for delayed sealing to suit the pressure cycle requirements In use, device 26 is configured to expand and contract due to changes in temperature thereof caused by one or both of the heat sinks 29. That is, as the device 26 "heats" it expands, and as the device 26 "cools" it contracts. In particular, as the respective heat sinks 29 coupled to the generator 28 and battery assembly 18 draw heat therefrom (i.e., heats sinks 29 "heat up"), the proximity of the device 26 with respect to the heat sinks 29 causes the device 26 to expand and draw air therein. The device 26 continues to expand until such time that the device 26 collapses onto itself. As the device 26 collapses, it expels air therefrom. The proximity of the device 26 with respect to the heat sinks 29 allows the expelled air to circulate around the heat sinks 29 and cool the heat sinks 29, which, in turn, cools the generator 28 and battery assembly 18; this process may be repeated for each subsequent use of the device 26.

The unique configuration of the device 26 overcomes the drawbacks typically associated with conventional portable surgical instruments. That is, the likelihood of the generator 18 and/or battery assembly "overheating" is reduced, if not, eliminated.

From the foregoing and with reference to the various figure drawings, those skilled in the art will appreciate that certain modifications can also be made to the present disclosure without departing from the scope of the same. For example, in some embodiments, it may prove advantageous to provide the devices 26, 126 adjacent other internal components of the respective forceps 2 and ultrasonic instrument 102. For example, it is within the purview of the present disclosure to have one or more devices 26, 126 adjacent the respective end effectors 12, 112. In this instance, the devices 26, 126 may be part of a micro-electromechanical system (MEMS) and may be implemented to maintain the respective jaw members 14, 16 and 114, 116 (or components associated therewith, e.g., seal plates) at a desired temperature. In this instance, one or more suitable heat sinks 29, 129 may be positioned in the vicinity of the devices 26, 126 and may be configured to function as described above.

Moreover, in some embodiments, devices 26, 126 may be coupled to heat sinks 29, 129, respectively, such that devices 26, 126 contact heat sinks 29, 129, thus, changing a contact area to heat sinks 29, 129. In this particular embodiment, as devices 26, 126 heat up, a shape and/or volume change occurs as described above. In this embodiment, however, devices 26, 126 changes the contact area to heat sinks 29, 129 to a localized contact due to bending (e.g., similar to blowing up a balloon that has been lying on a table). More specifically, as the contact area diminishes, the temperature of devices 26, 126 drops and the volume change returns back to the initial volume. The pumping occurs as stated using valving and a time lag of the heat absorption in the materials. Exhaust or intake or both can be routed to supply additional convective cooling.

Additionally, any of the aforementioned systems can be run as a closed loop refrigeration cycle with an addition of a suitable return loop, and/or, venturi's, and a refrigerant.

While devices 26, 126 have been described herein as being utilized with surgical instruments 2, 102 that utilize RF energy and ultrasonic energy, respectively, devices 26, 126 may be utilized with other types of surgical instruments. For example, devices 26, 126 may be utilized with surgical instruments that utilize laser or microwave energy to treat tissue. Moreover, devices 26, 126 are not limited to use with portable surgical instruments and/or endoscopic surgical instruments. For example, devices 26, 126 may be utilized with electrosurgical forceps, e.g., open, hemostat style or closed types, that are not battery powered, but still include one or more heat dissipating components, e.g., electrodes, dissecting elements, etc. As can be appreciated, certain modifications may need to be made to devices 26, 126 and/or the surgical instrument intended for use therewith.

Further, the bimetal strips may be snap acting to facilitate rapid pumping of a volume and assist with thermal timing of the pumping action relative to a temperature profile/heat cycle. As can be appreciated, a change in proximity due to heat distortion of the bi-metal may be used to change the heat gain of the pump.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A surgical instrument, comprising:
a housing including an elongated shaft extending distally therefrom;
an end effector assembly operably supported at a distal end of the elongated shaft;
a generator operably coupled to the housing and in operable communication with a battery assembly of the surgical instrument, the generator configured to convert electrical energy into at least one of RF, ultrasonic, laser and microwave energy to energize the end effector assembly; and
a thermally-activatable device in operable communication with at least one of the generator and the battery assembly, the thermally-activatable device configured to expand and contract due to changes in temperature thereof to promote air-flow around at least one of the generator and battery assembly, wherein the thermally-activatable device is a bi-metal pump made from at least two strips of metal that have been joined via one of riveting, brazing and welding.

2. A surgical instrument according to claim 1, wherein the metal is selected from the group consisting of steel, copper and brass.

3. A surgical instrument according to claim 1, wherein the at least two strips of metal are formed into a generally cylindrical drum configuration having sidewalls coupled to top and bottom walls.

4. A surgical instrument according to claim 3, wherein a heat sink is operably associated with each of the generator and battery assembly.

5. A surgical instrument according to claim 4, wherein expansion and contraction of the thermally-activatable device is caused by the heat sink such that expansion of the thermally-activatable device draws air therein and contraction of the thermally-activatable device expels air therefrom.

6. A surgical instrument according to claim 1, wherein at least two check-valves are operably coupled to the thermally-activatable device and are configured to allow an in-flow of air into the thermally-activatable device upon expansion thereof and are configured to allow an out-flow of air from the thermally-activatable device upon contraction thereof.

7. A surgical instrument according to claim 1, wherein the surgical instrument is an electro surgical device.

8. A surgical instrument according to claim 1, wherein the surgical instrument is an ultrasonic device.

9. A surgical instrument, comprising:
a housing including an elongated shaft extending distally therefrom;
an end effector operably supported at the distal end of the elongated shaft;
a generator operably coupled to the housing and in operable communication with a battery assembly of the surgical instrument, the generator configured to convert electrical energy into at least one of RF, ultrasonic, laser and microwave energy to energize the at end effector;
a heat sink operably associated with each of the generator and battery assembly; and
a thermally-activatable device disposed in the housing and in operable communication with the generator and the battery assembly, the thermally-activatable device responsive to temperature change caused by the heat sink and configured to promote air-flow around at least one of the generator and battery assembly, wherein the thermally-activatable device is a bi-metal pump made from at least two strips of metal that have been joined via one of riveting, brazing and welding.

10. A surgical instrument according to claim 9, wherein the metal is selected from the group consisting of steel, copper and brass.

11. A surgical instrument according to claim 9, wherein the at least two strips of metal are formed into a generally cylindrical drum configuration having sidewalls coupled to top and bottom walls.

12. A surgical instrument according to claim 9, wherein the thermally-activatable device is configured to expand and contract due to changes in temperature thereof caused by the heat sink such that expansion of the thermally-activatable device draws air therein and contraction of the thermally-activatable device expels air therefrom.

13. A surgical instrument according to claim 9, wherein at least two check-valves are operably coupled to the thermally-activatable device and are configured to allow an in-flow of air into the thermally-activatable device upon expansion thereof and are configured to allow an out-flow of air from the thermally-activatable device upon contraction thereof.

* * * * *